US007955598B2

(12) United States Patent
Yoshizaki et al.

(10) Patent No.: US 7,955,598 B2
(45) Date of Patent: Jun. 7, 2011

(54) THERAPEUTIC AGENT FOR CHRONIC ARTHRITIDES DISEASES OF CHILDHOOD-RELATED DISEASES

(75) Inventors: Kazuyuki Yoshizaki, Ashiya (JP); Norihiro Nishimoto, Minoo (JP); Masahiro Iwamoto, Oyama (JP); Seiji Minota, Tokyo (JP); Shumpei Yokota, Chigasaki (JP); Takako Miyamae, Yokohama (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 375 days.

(21) Appl. No.: 11/704,233

(22) Filed: Feb. 9, 2007

(65) Prior Publication Data

US 2007/0148169 A1 Jun. 28, 2007

Related U.S. Application Data

(62) Division of application No. 10/473,165, filed as application No. PCT/JP02/03312 on Apr. 2, 2002, now abandoned.

(30) Foreign Application Priority Data

Apr. 2, 2001 (JP) .................................. 2001-103627
Apr. 6, 2001 (JP) .................................. 2001-109131

(51) Int. Cl.
*A61K 39/395* (2006.01)
(52) U.S. Cl. ..................................... 424/144.1; 514/825
(58) Field of Classification Search ........................ None
See application file for complete search history.

(56) References Cited

U.S. PATENT DOCUMENTS

| 5,670,373 | A | 9/1997 | Kishimoto |
| 5,851,793 | A | 12/1998 | Kishimoto |
| 5,888,510 | A | 3/1999 | Kishimoto et al. |
| 6,428,979 | B1 | 8/2002 | Kishimoto |
| 6,692,742 | B1 * | 2/2004 | Nakamura et al. ......... 424/145.1 |
| 6,723,319 | B1 | 4/2004 | Ito et al. |
| 7,479,543 | B2 * | 1/2009 | Tsuchiya et al. ........... 530/387.1 |
| 2002/0187150 | A1 | 12/2002 | Mihara et al. |
| 2003/0236260 | A1 | 12/2003 | Shimojo et al. |
| 2006/0292147 | A1 | 12/2006 | Yoshizaki et al. |

FOREIGN PATENT DOCUMENTS

| EP | 0 628 639 A1 | 12/1994 |
| EP | 0 783 893 | 7/1997 |
| EP | 0 791 359 A1 | 8/1997 |
| EP | 0 983 767 A1 | 3/2000 |
| EP | 1 074 268 | 2/2001 |
| RU | 2 147 443 C1 | 4/2000 |
| WO | WO 95/09873 A1 | 4/1995 |
| WO | WO-96/18648 | 6/1996 |
| WO | WO 9749428 A1 * | 12/1997 |
| WO | WO-98/13383 | 4/1998 |
| WO | WO-99/48523 | 9/1999 |
| WO | WO 2004/096273 A1 | 11/2004 |

OTHER PUBLICATIONS

Hoshino et al., J Rheumatol. Feb. 1998;25(2):396-8.*
Horneff et al., "Treatment of refractory juvenile chronic arthritis by monoclonal CD4 antibodies: a pilot study in two children," Annals of the Rheumatic Diseases, 1995, 54:846-849.
Reiter et al., "Treatment of rheumatoid arthritis with monoclonal CD4 antibody M-T151. Clinical results and immunopharmacologic effects in an open study, including repeated administration," Arthritis Rheum., May 1991, 34(5):525-536. (Abstract, PubMed PMID:2025306).
Bendayan, J. Histochem. Cytochem., vol. 43, 1995, pp. 881-886.
Carroll et al., "Antagonism of the IL-6 Cytokine Subfamily—A Potential Strategy for More Effective Therapy in Rheumatoid Arthritis," Inflamm. Res., vol. 47, 1998, pp. 1-7.
De Benedetti et al., "Interleukin 6 Causes Growth Impairment in Transgenic Mice through a Decrease in Insulin-like Growth Factor-I", *Journal of Clinical Investigation*, vol. 99, No. 4, Feb. 1997, pp. 643-650.
De Benedetti et al., Arthritis and Rheumatism, vol. 52, No. 3, 2005, pp. 687-693.
Elliott et al., "Suppression of Fever and the Acute-Phase Response in a Patient With Juvenile Chronic Arthritis Treated With Monoclonal Antibody to Tumour Necrosis Factor-α (cA2)," British Journal of Rheumatology, vol. 36, 1997, pp. 589-593.
Hashkes et al., JAMA, vol. 294, 2005, pp. 1671-1684.
Hirata et al., J. Immunol., vol. 143, 1989, pp. 2900-2906.
Imazeki et al., "IL-6 functions in cynomolgus monkeys blocked by a humanized antibody to human IL-6 receptor", *International Journal of Immunopharmacology*, vol. 20, pp. 345-357, 1998.
Keul et al., "A Possible Role for Soluble IL-6 Receptor in the Pathogenesis of Systemic Onset Juvenile Chronic Arthritis", *Cytokine*, vol. 10, No. 9, pp. 729-734, 1998.
Lepore et al., "Study of IL-2, IL-6, TNF Alpha, IFN Gamma and Beta in the Serum and Synovial Fluid of Patients With Juvenile Chronic Arthritis," Clin. Exp. Rheumatology, vol. 12, No. 5, 1994, pp. 561-565.
Mangee et al., "Cytokines in Juvenile Rheumatoid Arthritis (JRA)", *Cytokine*, vol. 10, No. 6, Jun. 6, 1998, pp. 471-480.
Mihara et al., "Humanized Antibody to Human Interleukin-6 Receptor Inhibits the Development of Collagen Arthritis in Cynomolgus Monkeys", *Clinical Immunology*, vol. 98, No. 3, Mar. 2001, pp. 3,19-326.
Oen et al., "Interleukin 6 and Autoantibodies in Juvenile Rheumatoid Arthritis," J. rheumatology, vol. 20, No. 11, 1993, pp. 1949-1956.

(Continued)

*Primary Examiner* — Zachary Skelding
(74) *Attorney, Agent, or Firm* — Foley & Lardner LLP

(57) ABSTRACT

A therapeutic agent for chronic arthritides diseases of childhood-related diseases, for example chronic arthritides diseases of childhood, Still's disease and the like, comprising an interleukin-6 (IL-6) antagonist as an active ingredient.

9 Claims, No Drawings

OTHER PUBLICATIONS

Rooney et al., "Inflammatory Cytokine Responses in Juvenile Chronic Arthritis," Br. J. Rheumatology, vol. 34, No. 5, 1995, pp. 454-460.

Takagi et al., Blockage of Interleukin-6 Receptor Ameliorates Joint Disease in Murine Collagen-Induced Arthritis, *Arthritis and Rheumatism*, vol. 41, No. 12, Dec. 1998, pp. 2117-2121.

Take et al., "Successful Treatment With Aurranofin in a Patient With Elderly-Onset Still's Disease," J. Med., vol. 25, No. 6, 1994, pp. 393-397.

Wendling et al., "Treatment of Severe Rheumatoid Arthritis by Anti-Interleukin 6 Monoclonal Antibody," The Journal of Rheumatology, vol. 20, 1993, pp. 259-262.

Yoshizaki et al., "Therapy of Rheumatoid Arthritis by Blocking IL-6 Signal Transduction with a Humanized Anti-IL-6 Receptor antibody", *Springer Seminars in Immunopathology*, Springer, Berlin, Germany, vol. 20, No. 1/2, 1998, pp. 247-259.

Juvenile Rheumatoid Arthritis, *The Merck Manual*, 17$^{th}$ Ed., Sec. 19, Chapter 270, p. 2398, 1999.

Office Action in corresponding Chilean Application 1239-2004, 8 pages.

Dosa, Laszlo, "IL-6 Receptor Antibody Shows Promise for Juvenile Rheumatoid Arthritis," ACR 67$^{th}$ Annual Scientific Meeting: Abstract 1070, Oct. 2003, 1 page.

Nishimoto et al., "Toxicity, Pharmacokinetics, and Dose-Finding Study of Repetitive treatment with the Humanized Anti-Interleukin 6 Receptor Antibody MRA in Rheumatoid Arthritis. Phase I/II Clinical Study," The Journal of Rheumatology, 2003, 30(7):1426-1435.

Gallagher et al., "Juvenile rheumatoid arthritis," Current Opinion in Rheumatology, 1999, 11:372-376.

Arkachaisri et al., "Use of Biologics in the Treatment of Childhood Rheumatic Diseases," Current Rheumatology Reports, Current Science, Aug. 1, 2000, 2(4):330-336.

De Benedetti et al., "Is Systematic Juvenile Rheumatoid Arthritis an Interleukin 6 Mediated Disease?", Journal of Rheumatology, Feb. 1, 1998, 25(2):203-207.

Fishman et al., "The Effect of Novel Polymorphisms in the Interleukin-6 (IL-6) Gene on IL-6 Transcription and Plasma IL-6 Levels, and an Association with Systemic-Onset Juvenile Chronic Arthritis," Journal of Clinical Investigation, Oct. 1, 1998, 102(7):1369-1376.

Mangge et al., "Long-Term Follow-Up of Cytokines and Soluble Cytokine Receptors in Peripheral Blood of Patients with Juvenile Rheumatoid Arthritis," Journal of Interferon and Cytokine Research, Sep. 1999, 19(9):1005-1010.

Yilmaz et al., "Cytokine Levels in Serum of Patients with Juvenile Rheumatoid Arthritis," Clinical Rheumatology, Jan. 2001, 20(1):30-35.

Office Action dated Dec. 7, 2009, in corresponding EP 02 708 772.5, 7 pages.

Adams et al., "Update on the pathogenesis and treatment of systemic onset juvenile rheumatoid arthritis," Curr. Opin. Rheum., 2005, 17:612-616.

Bellomo, R., "The Cytokine Network in the Critically Ill," Anaesthesia and Intensive Care, Aug. 1992, 20(3):288-302.

Brewer et al., "Penicillamine and hydroxychloroquine in the treatment of severe juvenile rheumatoid arthritis," New England J. Med., May 15, 1986, 314(20):1269-1276.

Choi et al,. "Serum Cytokine Profiles in Patients with Adult Onset Still's Disease," The Journal of Rheumatology, 2003, 30(11):2422-2427.

Elliott et al., "Treatment of systemic juvenile chronic arthritis (JCA) with monoclonal anti-TNFα—Temporary control of systemic but not articular features of disease," Arthritis Rheum., 1994, 37:S276, two pages.

Knulst et al., "Cytokine detection and modulation in acute graft vs. host disease in mice," Mediators of Inflammation, 1994, 3:33-40.

Nowak et al., "Combination of Methotrexate and Prednizone Decreases Circulating Concentrations of Interleukin 1β and Interleukin 6 in Patients with Rheumatoid Arthritis: Poor Correlation of Cytokine Supression with Clinical Improvement," International Journal of Immunopathology and Pharmacology, 1999, 12(1):13-21.

Taga et al,. "GP130 and the Interleukin-6 Family of Cytokines," Annu. Rev. Immun., 1997;15:797-819.

Thompson et al., "Chemokine Receptor CCR4 on CD4+ T Cells in Juvenile Rheumatoid Arthritis Synovial Fluid Defines a Subset of Cells with Increased IL-4:IFN-γ mRNA Ratios," J. Immunol., Jun. 1, 2001, 166(11):6899-6906.

Ulich et al., "Intratracheal Injection of Endotoxin and Cytokines," American Journal of Pathology, May 1991, 138 (5):1097-1101.

Office Action issued on Mar. 9, 2011, in corresponding Norwegian application 2003 4388, 5 pages, with English translation, 3 pages.

De Benedetti et al., "Correlation of serum interleukin-6 levels with joint involvement and thrombocytosis in systemic juvenile rheumatoid arthritis," Arthritis and Rheumatism, Sep. 1991, 34(9):1158-1163.

* cited by examiner

THERAPEUTIC AGENT FOR CHRONIC ARTHRITIDES DISEASES OF CHILDHOOD-RELATED DISEASES

CROSS-REFERENCE TO RELATED PATENT APPLICATIONS

This Application is a Divisional of application Ser. No. 10/473,165 which entered U.S. national phase on Sep. 29, 2003, from PCT/JP02/03312 filed Apr. 2, 2002, which claims priority from Japanese patent applications 2001-109131 filed Apr. 6, 2001 and 2001-103627 filed Apr. 2, 2001. The entire content of the aforementioned applications are incorporated herein by reference.

FIELD OF THE INVENTION

The present invention relates to a therapeutic agent for "chronic arthritides diseases of childhood-related diseases" comprising an interleukin-6 (IL-6) antagonist as an active ingredient. Chronic arthritides diseases of childhood-related diseases include chronic arthritides diseases of childhood, Still's disease and the like.

BACKGROUND ART

IL-6 is a cytokine called B-cell stimulating factor 2 (BSF2) or interferon β2. IL-6 was discovered as a differentiation factor responsible for activation of B-lymphatic cells (Hirano, T. et al., Nature (1986) 324, 73-76). Thereafter, it was found to be a multifunctional cytokine that influences the function of various cells (Akira, S. et al., Adv. in Immunology (1993) 54, 1-78). IL-6 has been reported to induce the maturation of T lymphatic cells (Lotz, M. et al., J. Exp. Med. (1988) 167, 1253-1258).

IL-6 propagates its biological activity through two proteins on the cell. One is a ligand-binding protein, IL-6 receptor, with a molecular weight of about 80 kD to which IL-6 binds (Taga T. et al., J. Exp. Med. (1987) 166, 967-981; Yamasaki, K. et al., Science (1987) 241, 825-828). IL-6 receptor exists not only in a membrane-bound form that penetrates and is expressed on the cell membrane but also as a soluble IL-6 receptor consisting mainly of the extracellular region.

The other is non-ligand-binding membrane-bound protein gp130 with a molecular weight of about 130 kD that takes part in signal transduction. IL-6 and IL-6 receptor form an IL-6/IL-6 receptor complex, to which gp130 is bound, and thereby the biological activity of IL-6 is propagated into the cell (Taga et al., Cell (1989) 58, 573-581).

IL-6 antagonists are substances that inhibit the transduction of IL-6 biological activities. Up to now, there have been known antibodies to IL-6 (anti-IL-6 antibodies), antibodies to IL-6 receptor (anti-IL-6 receptor antibodies), antibodies to gp130 (anti-gp130 antibodies), reshaped IL-6, IL-6 or IL-6 receptor partial peptides, and the like.

Antibodies to IL-6 receptor have been described in a number of reports (Novick D. et al., Hybridoma (1991) 10, 137-146; Huang, Y. W. et al., Hybridoma (1993) 12, 621-630; International Patent Application WO 95-09873; French Patent Application FR 2694767; U.S. Pat. No. 5,216,128). A humanized PM-1 antibody was obtained by implanting the complementarity determining region (CDR) of a mouse antibody PM-1 (Hirata et al., J. Immunology (1989), one of anti-IL-6 receptor antibodies, 143, 2900-2906) into a human antibody (International Patent Application WO 92-19759).

Chronic arthritides diseases of childhood are diseases comprising mainly chronic arthritis that develops at less than 16 years of age and is the most prevalent disease among the collagen diseases that develop in children. Unlike rheumatoid arthritis (RA) in adults, they are not considered to be a homogeneous disease and have a variety of disease types, and therefore they tend to be dealt with as a disease entity different from rheumatoid arthritis in adults.

As the name of chronic arthritides diseases of childhood, "juvenile rheumatoid arthritis (JRA)" has been used in Japan according to the diagnostic criteria in the United States, whereas in Europe the term "juvenile chronic arthritis (JCA)" is mainly used. Recently, terms such as idiopathic chronic arthritis (ICA) and juvenile idiopathic arthritis (JIA) have been used.

The disease types of chronic arthritides diseases of childhood have been categorized in various ways. According to the American College of Rheumatology (ACR), they are divided, as arthritic diseases that develop in children less than 16 years old and persist for six weeks or longer, into three disease types: 1) systemic onset JRA, 2) polyarticular, 3) pauciarticular (ARA classification) (JRA Criteria Subcommittee of the Diagnostic and Therapeutic Criteria Committee of the American Rheumatism Association Arthritis Rheum 20 (Suppl): 195, 1977). In Europe, the European League Against Rheumatism (EULAR) has made a classification that states that, though it differs from the above ARA classification in that the duration of arthritis is three months or more and arthritis due to psoriasis, ankylosing spondylitis etc. has been excluded, the three disease types are similar (Bulletin 4, Nomenclature and classification of Arthritis in Children. Basel, National Zeitung AG, 1977).

Recently, a revision of the classification has been attempted, and the International League of Associations for Rheumatology (ILAR) proposed in 1995 a classification plan of Idiopathic Arthritides of Childhood (Fink C W, Proposal for the development of classification criteria for idiopathic arthritides of childhood. J. Rheumatol., 22: 1566 (1995)), and in 1997 the revision was proposed as an ILAR plan (Southwood T R, Classifying childhood arthritis, Ann. Rheum. Dis. 56: 79 (1997)). This classification provides division into: 1) systemic arthritis, 2) polyarthritis RF positive, 3) polyarthritis RF negative, 4) oligoarthritis, 5) extended oligoarthritis, 6) enthesitis related arthritis, 7) psoriatic arthritis, and 8) others.

Furthermore, the present inventors have proposed a method of classifying chronic arthritides diseases of childhood into:

1) Primary Chronic Arthritides of Childhood
    (1) SPRASH Syndrome (SPRASH: Spiking Fever, Pericarditis, Rash, Arthritis, Splenomegaly, Hepatomegaly)
    Starts with relaxation heat and efflorescence, and serositis and hepatomegaly are observed with concomitant onset of simultaneous or delayed arthritis, but at times arthritis may not be observed.
    (2) Idiopathic Chronic Arthritides of Childhood
    No underlying diseases are present, and arthritis is the key pathology.
        a) rheumatoid factor (RF)-positive type
        b) anti-nuclear antibody (ANA)-positive type
        c) RF/ANA-negative type
2) Secondary Chronic Arthritides of Childhood
    Genetic or nongenetic original diseases are accompanied by arthritis (Shunpei Yokota, "Advances in recent therapeutic methods for chronic arthritides diseases of childhood", Rheumatism, 39: 860 (1999)).

It has been reported that various cytokines are involved in chronic arthritides diseases of childhood. In particular, it is thought that imbalance in inflammatory cytokines IL-1, IL-6, IL-12 and TNF-α, and anti-inflammatory cytokines IL-1ra (IL-1 receptor antagonist), IL-10, IL-13, sTNFR (soluble TNF receptor) is associated with the disease.

For the treatment of chronic arthritides diseases of childhood, nonsteroidal anti-inflammatory drugs, corticosteroids, antirheumatic drugs (gold compounds etc.), immunosuppressants, methotrexate (MTX etc.) have been used. However, as the therapeutic effects differ with the patients, the development of more effective therapeutic regimens is being awaited.

Still's disease, first described by the British pediatrician Dr. Still in 1897, was reported to have a clinical picture clearly different from that of rheumatoid arthritis in adults and is a disease seen in children to adults (especially in adolescence and the main symptoms include fever, erythema, arthritis, serositis and the like. Among them, adult-onset type is designated as adult onset Still's disease. In Still's disease, rheumatoid factor is usually negative.

In children, Still's disease is another name of the systemic type of juvenile rheumatoid arthritis (juvenile rheumatoid arthritis (JRA), JCA (juvenile chronic arthritis), juvenile idiopathic arthritis (JIA)) which is a chronic arthritis developing in children at less than 16 years old. For the causes of Still's disease, environmental factors such as a virus, host factors such as HLA, and immunological abnormalities have been reported, but the etiology is still obscure.

Still's disease in adults and that in children are considered to be almost the same disease, though there are minor differences in clinical feature in addition to the age when the disease develops. Still's disease in children refers to JRA of the systemic type as described above. However, JRA and rheumatoid arthritis (RA) in adults are clinically different in many ways and are dealt with as different diseases, and therefore Still's disease in adults is often dealt with as an independent disease entity among the rheumatic diseases.

As diagnostic criteria for Still's disease in adults, there have been known those by Yamaguchi (Journal of Rheumatology 19(3): 424-30, 1992), Reginato (Seminars in Arthritis & Rheumatism 17(1): 39-57, 1987), Cush (Rheumatology Grand Rounds, University of Pittsburgh Medical Center; Jan. 30, 1984), Goldman (Southern Medical Journal 73: 555-563, 1980) and the like.

On the relationship between Still's disease and cytokines, association with cytokines such as IL-1, IL-2, IL-4, IL-6, IL-7, IL-8, IL-10, TNF-α, and IFN-γ has been reported, and among them, inflammatory cytokines such as IL-1, IL-6, TNF-α, and IFN-γ have been implicated in the pathology of Still's disease.

With respect to IL-6, de Benedetti et al. reported that serum levels of IL-6 are elevated in Still's disease in children (Arthritis Rheum. 34: 1158, 1991), and that a large amount of IL-6/soluble IL-6 receptor (sIL-6R) complex is present in the serum of patients with Still's disease in children and a correlation can be seen between this complex level and CRP values (J. Clin. Invest. 93: 2114, 1994). Furthermore, Rooney et al. have reported that plasma levels of IL-6 and TNF-α are elevated in patients with Still's disease in children (Br. J. Rheumatol. 34: 454, 1995).

As a method of treating Still's disease, nonsteroidal anti-inflammatory drugs, corticosteroids, antirheumatic drugs (gold compounds etc.), immunosuppressants, gamma globulin formulations, methotrexate (MTX etc.) have been used. However, as the therapeutic effects differ with the patients, the development of more effective therapeutic regimens is being sought after.

DISCLOSURE OF THE INVENTION

Thus, the present invention provides a novel therapeutic agent for chronic arthritides diseases of childhood-related diseases, said agent being of a type different from the conventional therapeutic agents for chronic arthritides diseases of childhood-related diseases. In accordance with the present invention, chronic arthritides diseases of childhood-related diseases included chronic arthritides diseases of childhood and Still's disease.

After intensive and extensive study to solve the above problems, the present inventors have found that an interleukin-6 (IL-6) antagonist has an effect of treating chronic arthritides diseases of childhood-related diseases, and have completed the present invention.

Thus, the present invention provides a therapeutic agent for chronic arthritides diseases of childhood-related diseases comprising an interleukin-6 (IL-6) antagonist as an active ingredient.

More specifically, the present invention provides a therapeutic agent for chronic arthritides diseases of childhood comprising an interleukin-6 (IL-6) antagonist as an active ingredient.

The present invention also provides a therapeutic agent for Still's disease comprising an interleukin-6 (IL-6) antagonist as an active ingredient.

BEST MODE FOR CARRYING OUT THE INVENTION

The above IL-6 antagonist is preferably an antibody against IL-6 receptor, and preferably a monoclonal antibody against human IL-6 receptor or a monoclonal antibody against mouse IL-6 receptor. As the above monoclonal antibody against human IL-6 receptor, there can be illustrated PM-1 antibody, and as the above monoclonal antibody against mouse IL-6 receptor, there can be illustrated MR16-1 antibody.

The above antibody is preferably a chimeric antibody, a humanized antibody or a human antibody and, for example, is a humanized PM-1 antibody.

Chronic arthritides diseases of childhood which are the subject of treatment with a therapeutic agent of the present invention include all diseases in the above ARA, EULAR, and ILAR classifications, and the classification by the present inventors. With the advance in the serological diagnostic methods and the advance in therapeutic methods, the disease type classification of chronic arthritides diseases of childhood is now undergoing a review on a global scale and it can be said to be in a state of uncertainty. Preferred treatment subjects, for the therapeutic agent of the present invention, are: in the ARA classification, systemic onset, polyarticular, and pauciarticular; in the EULAR classification, systemic onset, polyarticular, and oligoarticular; in the ILAR classification, systemic onset, polyarticular (RF positive), polyarticular (RF negative), oligoarthritis, and extended oligoarthritis; and, in the classification by the present inventors, primary chronic arthritides of childhood (SPRASH syndrome, idiopathic chronic arthritides of childhood (a. rheumatoid factor (RF)-positive type, b. anti-nuclear antibody (ANA)-positive type, c. RF/ANA-negative type)), and as most preferred subjects of treatment are: in the ARA classification, systemic onset and polyarticular; in the EULAR classification, systemic onset and polyarticular; in the ILAR classification, systemic onset, polyarticular (RF positive), polyarticular (RF negative), and extended oligoarthritis; and, in the classification by the present inventors, primary chronic arthritides of childhood (SPRASH syndrome, idiopathic chronic arthritides of childhood (a. rheumatoid factor (RF)-positive type, b. anti-nuclear antibody (ANA)-positive type)). More preferred subjects of treatment are: in the ARA classification, systemic onset and polyarticular; in the EULAR classification, systemic onset and polyarticular; in the ILAR classification, systemic onset, polyarticular (RF positive), and extended oligoarthritis; and, in the classification by the present inventors, primary chronic arthritides of childhood (SPRASH syndrome, idiopathic chronic arthritides of childhood (a. rheumatoid factor (RF)-positive type)).

IL-6 antagonists for use in the present invention may be of any origin, any type, and any form, as long as they exhibit therapeutic effects on chronic arthritides diseases of childhood-related diseases.

IL-6 antagonists are substances that block signal transduction by IL-6 and inhibit the biological activity of IL-6. IL-6 antagonists are substances that preferably have an inhibitory action on the binding to any of IL-6, IL-6 receptor or gp130. As IL-6 antagonists, there can be mentioned, for example, anti-IL-6 antibody, anti-IL-6 receptor antibody, ant-gp130 antibody, reshaped IL-6, soluble reshaped IL-6 receptor, or partial peptides of IL-6 or IL-6 receptor, as well as low molecular weight substances that exhibit activities similar to them.

Anti-IL-6 antibodies for use in the present invention can be obtained as polyclonal or monoclonal antibodies using a known method. As the anti-IL-6 antibodies for use in the present invention, monoclonal antibodies of, in particular, mammalian origin are preferred. Monoclonal antibodies of a mammalian origin include those produced by a hybridoma and those produced by a host which has been transformed by gene engineering technology with an expression vector containing the antibody gene. These antibodies, via binding to IL-6, block the binding of IL-6 to IL-6 receptor, and thereby block the propagation of biological activity of IL-6 into the cell.

Examples of such antibodies include MH166 antibody (Matsuda, et al., Eur. J. Immunology (1988) 18, 951-956), or SK2 antibody (Sato, et al., The 21st General Meeting of the Japanese Society for Immunology, Gakujutu Kiroku (1991) 21, 166) etc.

A hybridoma that produces anti-IL-6 antibody can be basically constructed using a known procedure as described bellow. Thus, IL-6 is used as a sensitizing antigen, which is immunized in the conventional method of immunization, and the immune cells thus obtained are fused with known parent cells in a conventional cell fusion process, followed by a conventional screening method to screen monoclonal antibody-producing cells.

Specifically, anti-IL-6 antibodies may be obtained in the following manner. For example, human IL-6 to be used as the sensitizing antigen for obtaining antibody can be obtained using the IL-6 gene/amino acid sequence disclosed in Eur. J. Biochem. (1987) 168, 543-550; J. Immunol. (1988) 140, 1534-1541, or Agr. Biol. Chem. (1990) 54, 2685-2688.

After the gene sequence of IL-6 was inserted into a known expression vector to transform a suitable host cell, the IL-6 protein of interest may be purified from the host cell or a culture supernatant thereof by a known method, and the purified IL-6 protein may be used as the sensitizing antigen. Alternatively, a fusion protein of the IL-6 protein and another protein may be used as the sensitizing antigen.

Anti-IL-6 receptor antibodies for use in the present invention can be obtained as polyclonal or monoclonal antibodies using a known method. As the anti-IL-6 receptor antibodies for use in the present invention, monoclonal antibodies of, in particular, a mammalian origin are preferred. Monoclonal antibodies of a mammalian origin include those produced by a hybridoma and those produced by a host which has been transformed by gene engineering technology with an expression vector containing the antibody gene. These antibodies, via binding to IL-6, block the binding of IL-6 to IL-6 receptor, and thereby block the propagation of biological activity of IL-6 into the cell.

Examples of such antibodies include MR16-1 antibody (Tamura, T. et al., Proc. Natl. Acad. Sci. USA (1993) 90, 11924-11928), PM-1 antibody (Hirata, Y. et al., J. Immunology (1989) 143, 2900-2906), AUK12-20 antibody, AUK64-7 antibody or AUK146-15 antibody (International Patent Application WO 92-19759), and the like. Among them, PM-1 antibody is most preferred.

Incidentally, the hybridoma cell line which produces PM-1 antibody has been internationally deposited under the provisions of the Budapest Treaty as PM-1 on Jul. 12, 1988 with the International Patent Organism Depository of the National Institute of Industrial Science and Technology (Central 6, 1-1-1 Higashi, Tsukuba City, Ibaraki Pref., 305-5466 Japan) as FERM BP-2998. Also, the hybridoma cell line which produces MR16-1 antibody has been internationally deposited under the provisions of the Budapest Treaty as Rat-mouse hybridoma MR16-1 on Mar. 13, 1997 with the International Patent Organism Depository of the National Institute of Industrial Science and Technology (Central 6, 1-1-1 Higashi, Tsukuba City, Ibaraki Pref., 305-5466 Japan) as FERM BP-5875.

A hybridoma that produces anti-IL-6 receptor monoclonal antibody can, basically, be constructed using a known procedure as described bellow. Thus, IL-6 receptor is used as a sensitizing antigen, which is immunized in the conventional method of immunization, and the immune cells thus obtained are fused with known parent cells in a conventional cell fusion process, followed by a conventional screening method to screen monoclonal antibody-producing cells.

Specifically, anti-IL-6 receptor antibodies may be obtained in the following manner. For example, human IL-6 receptor used as the sensitizing antigen for obtaining antibody can be obtained using the IL-6 receptor gene/amino acid sequence disclosed in European Patent Application No. EP 325474, and mouse IL-6 receptor can be obtained using the IL-6 receptor gene/amino acid sequence disclosed in Japanese Unexamined Patent Publication (Kokai) No. 3-155795.

There are two types of IL-6 receptor: IL-6 receptor expressed on the cell membrane, and IL-6 receptor detached from the cell membrane (Soluble IL-6 Receptor; Yasukawa et al., J. Biochem. (1990) 108, 673-676). Soluble IL-6 antibody is composed of the substantially extracellular region of IL-6 receptor bound to the cell membrane, and is different from the membrane-bound IL-6 receptor in that the former lacks the transmembrane region or both of the transmembrane region and the intracellular region. IL-6 receptor protein may be any IL-6 receptor, as long as it can be used as a sensitizing antigen for preparing anti-IL-6 receptor antibody for use in the present invention.

After a gene encoding IL-6 receptor has been inserted into a known expression vector system to transform an appropriate host cell, the desired IL-6 receptor protein may be purified from the host cell or a culture supernatant thereof using a known method, and the IL-6 receptor protein thus purified may be used as the sensitizing antigen. Alternatively, cells that express IL-6 receptor protein or a fusion protein of IL-6 receptor protein and another protein may be used as the sensitizing antigen.

*Escherichia coli* (*E. coli*) containing a plasmid pIBIBSF2R that comprises cDNA encoding human IL-6 receptor has been internationally deposited under the provisions of the Budapest Treaty as HB101-pIBIBSF2R on Jan. 9, 1989 with the International Patent Organism Depository of the National Institute of Industrial Science and Technology (Central 6, 1-1-1 Higashi, Tsukuba City, Ibaraki Pref., 305-5466 Japan) as FERM BP-2232.

Anti-gp130 antibodies for use in the present invention can be obtained as polyclonal or monoclonal antibodies using a known method. As the anti-gp130 antibodies for use in the present invention, monoclonal antibodies of, in particular, mammalian origin are preferred. Monoclonal antibodies of a mammalian origin include those produced by a hybridoma and those produced by a host which has been transformed by gene engineering technology with an expression vector containing the antibody gene. These antibodies, via binding to gp130, block the binding of gp130 to the IL-6/IL-6 receptor complex, and thereby block the propagation of biological activity of IL-6 into the cell.

Examples of such antibodies include AM64 antibody (Japanese Unexamined Patent Publication (Kokai) No. 3-219894), 4B11 antibody and 2H4 antibody (U.S. Pat. No. 5,571,513), B-S12 antibody and B-P8 antibody (Japanese Unexamined Patent Publication (Kokai) No. 8-291199) etc.

A hybridoma that produces anti-gp130 antibody can be basically constructed using a known procedure as described below. Thus, gp130 is used as a sensitizing antigen, which is immunized in the conventional method of immunization, and the immune cells thus obtained are fused with known parent cells in a conventional cell fusion process, followed by a conventional screening method to screen monoclonal antibody-producing cells.

Specifically, monoclonal antibodies may be obtained in the following manner. For example, gp130 used as the sensitizing antigen for obtaining antibody can be obtained using the gp130 gene/amino acid sequence disclosed in European Patent Application No. EP 411946.

The gene sequence of gp130 may be inserted into a known expression vector, and said vector is used to transform a suitable host cell. From the host cell or a culture supernatant therefrom, the gp130 protein of interest may be purified by a known method, and the purified IL-6 protein may be used as the sensitizing antigen. Alternatively, cells expressing gp130, or a fusion protein of the gp130 protein and another protein may be used as the sensitizing antigen.

Preferably, mammals to be immunized with the sensitizing antigen are selected in consideration of their compatibility with the parent cells for use in cell fusion and they generally include, but are not limited to, rodents such as mice, rats and hamsters.

Immunization of animals with a sensitizing antigen is carried out using a known method. A general method, for example, involves intraperitoneal or subcutaneous administration of a sensitizing antigen to the mammal. Specifically, a sensitizing antigen, which was diluted and suspended in an appropriate amount of phosphate buffered saline (PBS) or physiological saline etc., is mixed with an appropriate amount of a common adjuvant such as Freund's complete adjuvant. After being emulsified, it is preferably administered to a mammal several times every 4 to 21 days. Additionally, a suitable carrier may be used at the time of immunization of the sensitizing antigen.

After the immunization and confirmation of an increase in the desired antibody levels in the serum by a conventional method, immune cells are taken out from the mammal and are subjected to cell fusion. As preferred immune cells that are subjected to cell fusion, there can be specifically mentioned spleen cells.

Mammalian myeloma cells as the other parent cells which are subjected to cell fusion with the above-mentioned immune cells preferably include various known cell lines such as P3x63Ag8.653 (Kearney, J. F. et al., J. Immunol. (1979) 123, 1548-1550), P3x63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), R210 (Galfre, G. et al., Nature (1979) 217, 131-133) and the like, which may be used as appropriate.

Cell fusion between the above immune cells and myeloma cells may be essentially conducted in accordance with a known method such as is described in Milstein et al. (Kohler, G. and Milstein, C., Methods Enzymol. (1981) 73, 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and an adjuvant such as dimethyl sulfoxide may be added as desired to enhance the efficiency of fusion.

The preferred ratio of the immune cells and the myeloma cells for use is, for example, 1 to 10 times more immune cells than the myeloma cells. Examples of culture media to be used for the above cell fusion include, for example, RPMI 1640 medium and MEM culture medium suitable for the growth of the above myeloma cell lines, and the conventional culture medium used for this type of cell culture and, besides, a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of 1000 to 6000, is added at a concentration of 30 to 60% (w/v) and mixed to obtain the desired fusion cells (hybridomas). Then, by repeating a sequential addition of a suitable culture liquid and centrifugation to remove the supernatant, cell fusion agents etc., that are undesirable for the growth of the hybridoma, can be removed.

Said hybridoma is selected by culturing in the conventional selection medium, for example, HAT culture medium (a culture liquid containing hypoxanthine, aminopterin, and thymidine). Culturing in said HAT culture medium is continued generally for the period of time sufficient to effect killing of the cells other than the desired hybridoma (non-fusion cells), generally several days to several weeks. The conventional limiting dilution method is conducted in which the hybridomas producing the desired antibody are screened and cloned.

In addition to obtaining the above hybridoma by immunizing an animal other than the human with an antigen, it is also possible to sensitize human lymphocytes in vitro with the desired antigen protein or antigen-expressing cells, and the resulting sensitized B-lymphocytes are fused with a myeloma cell, for example U266, having the ability of dividing permanently to obtain a hybridoma that produces the desired human antibody having the activity of binding to the desired antigen or antigen-expressing cells (Japanese Post-examined Patent Publication (Kokoku) 1-59878). Furthermore, a transgenic animal having a repertoire of human antibody genes is immunized with the antigen or antigen-expressing cells to obtain the desired human antibody according to the above-mentioned method (see International Patent Application WO 93/12227, WO 92/03918, WO 94/02602, WO 94/25585, WO 96/34096 and WO 96/33735).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there can be used a method in which said hybridoma is cultured in the conventional method and the antibodies are obtained as the supernatant, or a method in which the hybridoma is implanted into and grown in a mammal compatible with said hybridoma and the antibodies are obtained as the ascites. The former method is suitable for obtaining high-purity antibodies, whereas the latter is suitable for a large scale production of antibodies.

For example, an anti-IL-6 receptor antibody-producing hybridoma can be polypeptide by a method disclosed in Japanese Unexamined Patent Publication (Kokai) No. 3-139293. There may be used a method in which The PM-1 antibody-producing hybridoma that has been internationally deposited under the provisions of the Budapest Treaty on Jul. 12, 1988 with the International Patent Organism Depository of the National Institute of Industrial Science and Technology (Central 6, 1-1-1 Higashi, Tsukuba City, Ibaraki Pref., 305-5466 Japan) as FERM BP-2998 is intraperitoneally injected to BALB/c mice to obtain ascites, from which ascites PM-1 antibody may be purified, or a method in which the hybridoma is cultured in a RPMI 1640 medium containing 10% bovine fetal serum, 5% BM-Codimed H1 (manufactured by Boehringer Mannheim), the hybridoma SFM medium (manufactured by GIBCO BRL), the PFHM-II medium (manufactured by GIBCO BRL) or the like, from the culture supernatant of which PM-1 antibody may be purified.

In accordance with the present invention, as monoclonal antibody, there can be used a recombinant antibody that was produced by cloning an antibody gene from a hybridoma and the gene is then integrated into an appropriate vector, which is introduced into a host to produce the recombinant antibody using gene recombinant technology (see, for example, Borrebaeck, C. A. K. and Larrick, J. W., THERAPEUTIC MONOCLONAL ANTIBODIES, published in the United Kingdom by MACMILLAN PUBLISHERS LTD. 1990).

Specifically, mRNA encoding the variable region (V region) of the antibody is isolated from the cell that produces the antibody of interest, for example a hybridoma. The isolation of mRNA is conducted by preparing total RNA by a known method such as the guanidine ultracentrifuge method (Chirgwin, J. M. et al., Biochemistry (1979) 18, 5294-5299), the AGPC method (Chomczynski, P. et al., Anal. Biochem. (1987) 162, 156-159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) which employs PCR may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The base sequence of the desired DNA may be confirmed by a known method such as the dideoxy method.

Once DNA encoding the V region of the desired antibody has been obtained, it may be ligated to DNA encoding the constant region (C region) of the desired antibody, which is then integrated into an expression vector. Alternatively, DNA encoding the V region of the antibody may be integrated into an expression vector which already contains DNA encoding the C region of the antibody.

In order to produce antibody for use in the present invention, the antibody gene is integrated into an expression vector so as to be expressed under the control of the expression regulatory region, for example an enhancer and/or a promoter. Subsequently, the expression vector is transformed into a host cell and the antibody can then be expressed therein.

In accordance with the present invention, artificially altered recombinant antibodies such as chimeric antibody, humanized antibody and human antibody can be used for the purpose of lowering heterologous antigenicity against humans. These altered antibody can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Application WO 92-19759). Using this known method, chimeric antibody useful for the present invention can be obtained.

Plasmids containing the L chain V region or the H chain V region of chimeric PM-1 antibody have each been designated as pPM-k3 and pPM-h1, respectively, and E. coli having a respective plasmid has been internationally deposited under the provisions of the Budapest Treaty as NCIMB40366 and NCIMB40362 on Feb. 11, 1991 with the National Collections of Industrial and Marine Bacteria Limited.

Humanized antibody which is also called reshaped human antibody has been made by implanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Application WO 92-19759).

Specifically, a DNA sequence which was designed to ligate the CDR of mouse antibody with the framework region (FR) of human antibody is synthesized from several divided oligonucleotides having sections overlapping with one another at the ends thereof. The DNA thus obtained is ligated to DNA encoding the C region of human antibody and then is incorporated into an expression vector, which is introduced into a host for antibody production (see European Patent Application EP 239400 and International Patent Application WO 92-19759).

For the FR of human antibody ligated through CDR, the CDR that has a favorable antigen-binding site is selected. When desired, amino acids in the FR of antibody V region may be substituted so that the CDR of humanized antibody may form an appropriate antigen biding site (Sato, K. et al., Cancer Res. (1993) 53, 851-856).

As the C region of human antibody, there can be used, for example, $C\gamma 1$, $C\gamma 2$, $C\gamma 3$, or $C\gamma 4$. The C region of human antibody may also be modified in order to improve the stability of antibody and of the production thereof.

Chimeric antibody consists of the V region of antibody of a human origin other than humans and the C region of human antibody, and humanized antibody consists of the complementarity determining region of antibody of a human origin other than humans and the framework region and the C region of human antibody, with their antigenicity in the human body being decreased, and thus are useful as antibody for use in the present invention.

As a preferred embodiment of humanized antibody for use in the present invention, there can be mentioned humanized PM-1 antibody (see International Patent Application WO 92-19759).

As a method of obtaining human antibody, in addition to those described above, there is known a method of obtaining human antibody by means of panning. For example, the variable region of human antibody is expressed on the surface of a phage by the phage display method as a single chain antibody (scFv) to select a phage that binds to the antigen. By analyzing the gene of the phage selected, the DNA sequence encoding the variable region of the human antibody that binds to the antigen can be identified. Once the DNA sequence of scfv that binds to the antigen has been clarified, said sequence can be used to prepare a suitable expression vector and human antibody can be obtained. These methods are already known and can be found in WO 92/01047, WO 92/20791, WO 93/06213, WO 93/11236, WO 93/19172, WO 95/01438, and WO 95/15388.

Antibody genes constructed as mentioned above may be expressed and obtained in a known manner. In the case of mammalian cells, expression may be accomplished using a DNA in which a commonly used useful promoter, an antibody gene to be expressed, and the poly A signal have been operably linked at 3' downstream thereof, or a vector containing it. As the promoter/enhancer, for example, there can be mentioned human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Mulligan, R. C. et al., Nature (1979) 277, 108-114) when SV40 promoter/enhancer is used, and by the method of Mizushima, S. et al. (Mizushima, S. and Nagata, S., Nucleic Acids Res. (1990) 18, 5322) when HEF1α promoter/enhancer is used.

In the case of *E. coli*, expression may be conducted by operably linking a commonly used promoter, a signal sequence for antibody secretion, and an antibody gene to be expressed, followed by expression thereof. As the promoter, for example, there can be mentioned lacz promoter and araB promoter. The method of Ward et al. (Ward, E. S. et al., Nature (1989) 341, 544-546; Ward, E. S. et al., FASEB J. (1992) 6, 2422-2427) may be used when lacz promoter is used, and the method of Better et al. (Better, M. et al., Science (1988) 240, 1041-1043) may be used when araB promoter is used.

As a signal sequence for antibody secretion, when produced in the periplasm of *E. coli*, the pelB signal sequence (Lei, S. P. et al., J. Bacteriol. (1987) 169, 4379-4383) can be used. After separating the antibody produced in the periplasm, the structure of the antibody is appropriately refolded before use (see, for example, WO 96-30394).

As the origin of replication, there can be used those derived from SV40, polyoma virus, adenovirus, bovine papilloma virus (BPV), and the like. Furthermore, for amplification of the gene copy number in the host cell system, expression vectors can include, as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene, and the like.

For the production of antibody for use in the present invention, any production system can be used, and the production systems of antibody preparation comprise the in vitro or the in vivo production system. As the in vitro production systems, there can be mentioned a production system which employs eukaryotic cells and the production system which employs prokaryotic cells.

When eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus* oocytes, or (3) insect cells such as sf9, sf21, and Tn5. Known plant cells include, for example, those derived from the Nicotiana tabacum which is subjected to callus culture. Known fungal cells include yeasts such as genus *Saccharomyces*, more specifically *Saccharomyces cereviceae*, or filamentous fungi such as the *Aspergillus* family, more specifically *Aspergillus niger*.

When prokaryotic cells are used, there are the production systems which employ bacterial cells. Known bacterial cells include *Escherichia coli*, and *Bacillus subtilis*.

By introducing, via transformation, the gene of the desired antibody into these cells and culturing the transformed cells in vitro, the antibody can be obtained. Culturing is conducted in the known methods. For example, as the culture liquid for mammalian cells, DMEM, MEM, RPMI1640, IMDM and the like can be used, and serum supplements such as fetal calf serum (FCS) may be used in combination. In addition, antibodies may be produced in vivo by implanting cells into which the antibody gene has been introduced into the abdominal cavity of an animal, and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also, as insects, silkworms can be used and, in the case of plants, tobacco, for example, can be used.

Antibody genes are introduced into these animals and plants, in which the genes are produced and then collected. For example, antibody genes are inserted into the middle of the gene encoding protein which is inherently produced in the milk such as goat β casein to prepare fusion genes. DNA fragments containing the fusion gene into which the antibody gene has been inserted are injected to a goat embryo, and the embryo is introduced into a female goat. The desired antibody is obtained from the milk produced by a transgenic goat produced by the goat that received the embryo or the offspring thereof. In order to increase the amount of milk containing the desired antibody produced by the transgenic goat, hormones may be given to the transgenic goat as appropriate (Ebert, K. M. et al., Bio/Technology (1994) 12, 699-702).

When silkworms are used, the silkworm is infected with a baculovirus into which desired antibody gene has been inserted, and the desired antibody can be obtained from the body fluid of the silkworm (Maeda, S. et al., Nature (1985) 315, 592-594). Moreover, when tobacco is used, the desired antibody gene is inserted into an expression vector for plants, for example pMON 530, and then the vector is introduced into a bacterium such as Agrobacterium tumefaciens. The bacterium is then used to infect tobacco such as Nicotiana tabacum to obtain the desired antibody from the leaves of the tobacco (Julian, K. -C. Ma et al., Eur. J. Immunol. (1994) 24, 131-138).

When antibody is produced in an in vitro or in vivo production systems, as mentioned above, DNA encoding the heavy chain (H chain) or light chain (L chain) of antibody is separately incorporated into an expression vector and the hosts are transformed simultaneously, or DNA encoding the H chain and the L chain of antibody is integrated into a single expression vector and the host is transformed therewith (see International Patent Application WO 94-11523).

Antibodies for use in the present invention may be fragments of antibody or modified versions thereof as long as they are preferably used in the present invention. For example, as fragments of antibody, there may be mentioned Fab, F(ab')2, Fv or single-chain Fv (scFv) in which Fv's of H chain and L chain were ligated via a suitable linker.

Specifically antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods Enzymol. (1989) 178, 476-496; Plucktrun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. et al., TI BTECH (1991) 9, 132-137).

scfv can be obtained by ligating the V region of H chain and the V region of L chain of antibody. In the scFv, the V region of H chain and the V region of L chain are preferably ligated via a linker, preferably a peptide linker (Huston, J. S. et al., Proc. Natl. Acad. Sci. U.S.A. (1988) 85, 5879-5883). The V region of H chain and the V region of L chain in the scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the-template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scfv are constructed, an expression vector containing them and a host transformed with said expression vector can be obtained by a conventional method, and scFv can be obtained using the resultant host by a conventional method.

These antibody fragments can be produced by obtaining the gene thereof in a similar manner to that mentioned above, and by allowing it to be expressed in a host. "Antibody" as used in the present invention encompasses these antibody fragments.

As modified antibodies, antibodies associated with various molecules such as polyethylene glycol (PEG) can be used. "Antibody" as used in the present invention encompasses these modified antibodies. These modified antibodies can be obtained by chemically modifying the antibodies thus obtained. These methods have already been established in the art.

Antibodies expressed and produced as described above can be separated from inside or outside of the cell or from the host and then may be purified to homogeneity. Separation and purification of antibody for use in the present invention may be accomplished by affinity chromatography. As the column used for affinity chromatography, there can be mentioned Protein A column and Protein G column. Examples of carriers for use in Protein A column include, for example, Hyper D, POROS, Sepharose F.F. (Pharmacia) and the like. In addition, commonly used methods of separation and purification for proteins can be used, without any limitation.

Chromatography other than the above affinity chromatography, filters, gel filtration, salting out, dialysis and the like may be selected and combined as appropriate, in order to separate and purify the antibodies for use in the present invention. Chromatography includes, for example, ion exchange chromatography, hydrophobic chromatography, gel-filtration and the like. These chromatographies can be applied to high performance liquid chromatography (HPLC). Also, reverse phase HPLC (rpHPLC) may be used.

The concentration of antibody obtained as above can be determined by measurement of absorbance or by ELISA and the like. Thus, when absorbance measurement is employed, the antibody obtained is appropriately diluted with PBS(−) and then the absorbance is measured at 280 nm, followed by calculation using the absorption coefficient of 1.35 OD at 1 mg/ml. When ELISA is used, measurement is conducted as follows. Thus, 100 μl of goat anti-human IgG antibody (manufactured by TAGO) diluted to 1 μg/ml in 0.1 M bicarbonate buffer, pH 9.6, is added to a 96-well plate (manufactured by Nunc), and is incubated overnight at 4° C. to immobilize the antibody. After blocking, 100 μl each of appropriately diluted antibody for use in the present invention or samples containing the antibody, or human IgG (manufactured by CAPPEL) as the standard is added, and incubated at room temperature for 1 hour.

After washing, 100 μl of 5000-fold diluted alkaline phosphatase-labeled anti-human IgG antibody (manufactured by BIO SOURCE) is added, and incubated at room temperature for 1 hour. After washing, the substrate solution is added and incubated, followed by measurement of absorbance at 405 nm using the MICROPLATE READER Model 3550 (manufactured by Bio-Rad) to calculate the concentration of the desired antibody.

Reshaped IL-6 for use in the present invention is a substance that has an activity of binding with IL-6 receptor and that does not propagate the biological activity of IL-6. Thus, though reshaped IL-6 competes with IL-6 for binding to IL-6 receptor, it does not propagate the biological activity of IL-6, and therefore reshaped IL-6 blocks signal transduction by IL-6.

Reshaped IL-6 may be prepared by introducing mutations by replacing amino acid residues of the amino acid sequence of IL-6. IL-6 from which reshaped IL-6 is derived may be of any origin, but it is preferably human IL-6 considering antigenicity etc.

Specifically, the secondary structure of the amino acid sequence of IL-6 may be estimated using a known molecular modeling program such as WHATIF (Vriend et al., J. Mol. Graphics (I1990) 8, 52-56), and its effect on the overall amino acid residues to be replaced is evaluated. After determining suitable amino acid residues, mutation may be introduced using a vector containing a base sequence encoding human IL-6 gene as a template in a commonly used PCR method so as to replace amino acids, and thereby to obtain a gene encoding reshaped IL-6. This may be integrated, as appropriate, into a suitable expression vector to obtain reshaped IL-6 according to the above-mentioned methods for expression, production, and purification of recombinant antibody.

Specific examples of reshaped IL-6 has been disclosed in Brakenhoff et al., J. Biol. Chem. (1994) 269, 86-93, Saviono et al., EMBO J. (1994) 13, 1357-1367, WO 96-18648 and WO 96-17869.

Partial peptides of IL-6 or partial peptides of IL-6 receptor for use in the present invention are substances that have an activity of binding to IL-6 receptor or IL-6, respectively, and that do not propagate the biological activity of IL-6. Thus, partial peptides of IL-6 or partial peptides of IL-6 receptor bind to and capture IL-6 receptor or IL-6, respectively, so as to inhibit specifically the binding of IL-6 to IL-6 receptor. As a result, they do not allow propagating of the biological activity of IL-6, and thereby block signal transduction by IL-6.

Partial peptides of IL-6 or partial peptides of IL-6 receptor are peptides are peptides comprising part or all of the amino acid sequence involved in the binding of IL-6 and IL-6 receptor in the amino acid sequences of IL-6 or IL-6 receptor. Such peptides comprise usually 10-80 amino acid residues, preferably 20-50 amino acid residues, and more preferably 20-40 amino acid residues.

Partial peptides of IL-6 or partial peptides of IL-6 receptor specify the regions involved in the binding of IL-6 and IL-6 receptor in the amino acid sequence of IL-6 or IL-6 receptor, and part or all of the amino acid sequence can be prepared by a commonly known method such as gene engineering technology or peptide synthesis.

In order to prepare partial peptides of IL-6 or partial peptides of IL-6 receptor by gene engineering technology, a DNA sequence encoding the desired peptide can be integrated into an expression vector so that they may be obtained according to the above-mentioned methods for expression, production, and purification of recombinant antibody.

In order to prepare partial peptides of IL-6 or partial peptides of IL-6 receptor by peptide synthesis, a commonly used method in peptide synthesis such as solid-phase synthesis or liquid-phase synthesis can be used.

Specifically, methods described in "Zoku Iyakuhinno Kaihatsu, Vol. 14: Peptide Synthesis" edited by Haruaki Yajima, Hirokawa Shoten, 1991, can be used. As the solid-phase synthesis, there can be used a method in which an amino acid corresponding to the C-terminal of the peptide to be synthesized is bound to a support insoluble in organic solvents, and then a reaction in which amino acids of which α-amino group and a side chain functional group has been protected with a suitable protecting group is condensed one by one in the direction of from the C-terminal to the N-terminal and a reaction in which said protecting group of the α-amino group of the amino acid or the peptide bound to the resin is eliminated therefrom are alternately repeated to extend the peptide chain. The solid-phase peptide synthesis is roughly divided in the Boc method and the Fmoc method depending on the type of protecting groups used.

After thus synthesizing the peptide of interest, a deprotecting reaction or a cleavage reaction of the peptide chain from the support may be performed. For the cleavage reaction of peptide chains, the Boc method employs hydrogen fluoride or trifluoromethanesulfonic acid, or the Fmoc method usually employs TFA. In the Boc method, the above protected peptide resin is treated in the presence of anisole in hydrogen fluoride. Subsequently, the elimination of the protecting group and the cleavage from the support may be performed to collect the peptide. Lyophilization of this yields crude peptide. On the other hand, in the Fmoc method, the deprotection reaction and the cleavage reaction of the peptide chain from the support may be performed in a manner similar to the one mentioned above.

The crude peptide obtained may be subjected to HPLC to separate and purify it. In its elution, a water-acetonitrile solvent commonly used in protein purification may be used under an optimal condition. Fractions corresponding to the peaks of the chromatographic profile are harvested and then lyophilized. For the peptide fractions thus purified, molecular weight analysis by mass spectroscopy, analysis of amino acid composition, or analysis of amino acid sequence is performed for identification.

Specific examples of IL-6 partial peptides and IL-6 receptor partial peptides have been disclosed in Japanese Unexamined Patent Publication (Kokai) No. 2-188600, Japanese Unexamined Patent Publication (Kokai) No. 7-324097, Japanese Unexamined Patent Publication (Kokai) No. 8-311098, and U.S. Pat. No. 5,210,075.

The inhibitory activity of IL-6 signal transduction by IL-6 antagonist of the present invention can be evaluated using a commonly known method. Specifically, IL-6-dependent human myeloma line (S6B45, KPMM2), human Lennert T lymphoma line KT3, or IL-6-dependent HN60.BSF2 cells are cultured, to which IL-6 is added, and at the same time, in the presence of IL-6 antagonist, the incorporation of $^3H$ labeled thymidine by the IL-6 dependent cells is determined. Alternatively, $^{125}I$-labeled IL-6 and IL-6 antagonist, at the same time, are added, and then $^{125}I$-labeled IL-6 that bound to the IL-6-ecpressing cells is determined for evaluation. In the above assay system, in addition to the group in which the IL-6 antagonist is present, a negative control group in which contains no IL-6 antagonist is set up, and the results obtained in both are compared to evaluate the IL-6-inhibiting activity by IL-6 antagonist.

As shown in Examples below, as therapeutic effects was observed by administration of anti-IL-6 receptor antibody to children suffering from chronic arthritis, IL-6 antagonists such as anti-IL-6 receptor antibody were shown to have a therapeutic effect for chronic arthritides of childhood-related diseases.

Subjects to be treated in the present invention are mammals. The subject mammals to be treated are preferably humans.

Therapeutic agents for chronic arthritides of childhood-related diseases of the present invention may be administered orally or parenterally and systemically or locally. For example, intravenous injection such as drip infusion, intramuscular injection, intraperitoneal injection, subcutaneous injection, suppositories, enema, oral enteric coated tablets, and the like may be selected, and the dosage regimen may be selected as appropriate depending on the age and conditions of the patient. The effective dose is chosen from the range of 0.01 mg to 100 mg per kg of body weight per administration. Alternatively, the dosage of 1 to 1000 mg, preferably 5 to 50 mg per patient may be selected.

Preferable dose and method for administering is, for example in the case of anti-IL6 receptor antibody, an effective dose that provides free antibody in the blood, and specifically, 0.5 mg to 40 mg, and preferably 1 mg to 20 mg per 1 kg body weight per month (four weeks), which is administered at once, or divided to several parts and administered, for example, twice/week, once/week, once/two weeks, once/four weeks, etc, for example intravenously for example by dripping, or subcutaneously. Administering schedule may be adjusted by elongating intervals from twice/week or once/ week to once/two weeks, once/three weeks, once/four weeks, etc, dependent on observation of symptoms, and blood test profile.

Therapeutic agents for chronic arthritides of childhood-related diseases of the present invention may contain pharmaceutically acceptable carriers and additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, pharmaceutically acceptable surfactants and the like. Actual additives used are chosen from, but not limited to, the above or combinations thereof depending on the dosage form.

EXAMPLES

The present invention will be explained more specifically below with reference to Working Examples and Reference Examples, but it is to be noted that the present invention is not limited by these examples in any way.

Working Example 1

A patient (5 years old, male) with systemic-onset type juvenile rheumatoid arthritis having the following history was subjected to a MRA (humanized anti-IL-6 receptor antibody) treatment.
History Before the Treatment Symptoms developed with relaxation heat (one-peak fever at about 40° C. for consecutive days), arthralgia at both knees, and anthema. After diagnosing based on leukocytosis, negative anti-nuclear antibody, negative rheumatoid factor, increased erythrocyte sedimentation rate, high CRP levels, etc., an aspirin administration was started, but no improvement in relaxation heat and arthralgia was observed and the general condition was aggravated. Thus, it was changed to an oral bolus administration of steroid (prednisolone 30 mg/day) to see an improvement in various symptoms. However, with the gradual decrease in prednisolone, symptoms recurred at 10 mg/day, the patient was rehospitalized, subjected to a methylprednisolone (mPSL) pulse therapy and plasmapheresis, and furthermore the combined use of cyclosporin A (Cs A) was carried out with no improvement. Symptoms were severe (leukocyte count 25400/µl, CRP 11.2 mg/dL), and a plasmapheresis+mPSL pulse therapy+Cs A was carried out and the patient entered into remission. As an aftertreatment, prednisolone+froben was given to control relaxation heat, and a decline in fever was clinically noted, but inflammation-related hematology tests remained at high values (CRP>5 mg/dL), and after discharge from hospital, relaxation heat was periodically observed, but treatment and observation were continued mainly on an ambulatory basis. However, the patient started to complain of backache that was aggravated by fever, and after close examination using MBI etc., destructive damages were noted in the fourth and the fifth thoracic vertebras suggesting that they are compression fracture. Due to the necessity of relief to the thoracic vertebras, bed rest was continued for about one year, and accordingly muscles of the lower limbs have markedly weakened which rendered walking completely impossible. The triadic therapy of prednisolone+froben+Cs A was continued but CRP never dropped to 5 mg/dL or lower.
The Result of Treatment Administration started at 2 mg/kg. Since no side effects were seen, the dosage was increased to 4 mg/kg in a once per week administration. Fever that had been noted until then disappeared quickly, and about two weeks later CRP became negative. General malaise was cleared, and the patient somewhat improved. It became possible to decrease prednisolone gradually and has decreased to 1 mg/day.

From the above results, MRA was found to be effective for the treatment of chronic arthritides diseases of childhood of which symptoms could not be controlled even with nonsteroidal anti-inflammatory drugs such as aspirn and froben, long term bolus steroids (for example prednine and medrol), and immunosuppressants such as cyclosporin A and methotrexate. Therefore, it can be said that IL-6 antagonist, in particular anti-IL-6 receptor antibody, is effective as a therapeutic agent for chronic arthritides diseases of childhood, specifically the systemic onset type of the ARA classification, the systemic onset type of the EULAR classification, the systemic onset type of the ILAR classification, and the SPRASH syndrome of the present inventors' classification.

Working Example 2

A 22-year old female. In April 1998, erythema punctatum appeared at the femur, the recordial region, and fingers, and in May, arthralgia at the shoulder, the elbow and the knee, and fever between 38 and 39° C. appeared. Though nonsteroidal anti-inflammatory drugs (NSAIDs) were started, fever persisted, and in July, with leukocyte count at 18100/µl, CRP at 18.3 mg/dl, and serum ferritin at 440 ng/ml, the patient was diagnosed as having adult Still's disease. From early January 2000, fever between 39 and 40° C. and arthralgia appeared, which were believed to be a flare-up of adult Still's disease (CRP 15.8 mg/dl, ferritin, 205.8 ng/ml).

Since it was difficult to reduce the dosage of steroids, methotrexate (MTX) and cyclosporin A (Cs A) were used in combination, but this could not control the progress of the disease, which aggravated breathing, and thus the patient was placed under the control of artificial respiration. Though the disease was somewhat improved by a steroid therapy, a treatment with humanized anti-IL-6 receptor antibody (MRA) was started because of the complication of severe osteoporosis. MRA (200 mg) was intravenously drip-infused for every two weeks. The inflammatory reaction became negative on day 6 after the administration, and decreases in the amount of corticosteroids progressed smoothly, and no severe side effects were observed.

From the above results, MRA was found to be effective for the treatment of adult Still's disease of which symptoms could not be controlled even with the combined use of MTX and CsA. Therefore, it can be said that IL-6 antagonist, in particular anti-IL-6 receptor antibody, is effective as a therapeutic agent for Still's disease, specifically adult Still's disease.

Reference Example 1

Preparation of Human Soluble IL-6 Receptor

Using a plasmid pBSF2R.236 containing cDNA that encodes IL-6 receptor obtained by the method of Yamasaki et al. (Yamasaki et al., Science (1988) 241, 825-828), soluble IL-6 receptor was prepared by the PCR method. The plasmid pBSF2R.236 was digested with a restriction enzyme Sph I to obtain IL-6 receptor cDNA, which was inserted into mp18 (manufactured by Amersham). Using a synthetic primer designed to introduce a stop codon into IL-6 receptor cDNA, mutation was introduced into IL-6 receptor cDNA by the PCR method in an in vitro mutagenesis system (manufactured by Amersham). By this procedure, the stop codon was introduced at the position of amino acid 345, and cDNA encoding soluble IL-6 receptor was obtained.

In order to express soluble IL-6 receptor in CHO cells, it was ligated to a plasmid pSV (manufactured by Pharmacia) to obtain a plasmid pSVL344. Soluble IL-6 receptor cDNA digested with HindIII-SalI was inserted into a plasmid pECEdhfr containing the cDNA of dhfr to obtain a CHO cell-expressing plasmid pECEdhfr344.

Ten μg of plasmid pECEdhfr344 was transfected to a dhfr-CHO cell line DXB-11 (Urlaub, G. et al., Proc. Natl. Acad. Sci. USA (1980) 77, 4216-4220) by the calcium phosphate precipitation method (Chen, C. et al., Mol. Cell. Biol. (1987) 7, 2745-2751). The transfected CHO cells were cultured for three weeks in a nucleoside-free αMEM selection medium containing 1 mM glutamine, 10% dialyzed FCS, 100 U/ml penicillin and 100 μ/ml streptomycin.

The selected CHO cells were screened by the limiting dilution method to obtain a single CHO cells clone. The CHO cell clone was amplified with 20 nM-200 nM of methotrexate to investigate a human soluble IL-6 receptor-producing CHO cell line 5E27. The CHO cell line 5E27 was cultured in a Iscov modified Dulbecco medium (IMDM, manufactured by Gibco) supplemented with 5% FBS. The culture supernatant was collected and the concentration of soluble IL-6 receptor in the culture supernatant was determined by ELISA. The result confirmed the presence of soluble IL-6 receptor in the culture supernatant.

Reference Example 2

Preparation of Anti-human IL-6 Antibody

Ten μg of tissue-type IL-6 (Hirano et al., Immunol. Lett. (1988) 17, 41) was used with Freund's complete adjuvant to immunize BALB/c mice, and this was repeated every week until anti-IL-6 antibody can be detected in the serum. Immune cells were removed from the local lymph nodes, and were fused with a myeloma cell line P3U1 using polyethylene glycol 1500. Hybridomas were selected by the method of Oi et al. (Selective Methods in Cellular Immunology, W.H. Freeman and Co., San Francisco, 351, 19080) using the HAT culture medium to establish a hybridoma producing anti-human IL-6 antibody.

The hybridoma producing anti-human IL-6 antibody was subjected to an IL-6 binding assay in the following manner. Thus, a 96-well microtiter plate (manufactured by Dynatech Laboratories, Inc., Alexandria, Va.) made of flexible polyvinyl was coated overnight with 100 μl of goat anti-mouse Ig (10 μl/ml, manufactured by Cooper Biomedical, Inc., Malvern, Pa.) in 0.1 M carbonate hydrogen carbonate buffer (pH 9.6) at 4° C. Then, the plate was treated in 100 μl of PBS containing 1% bovine serum albumin (BSA) at room temperature for 2 hours.

After the plate was washed in PBS, 100 μl of the hybridoma culture supernatant was added to each well, and incubated overnight at 4° C. After washing the plate, $^{125}$I-labelled recombinant type IL-6 was added to each well to 2000 cpm/0.5 ng/well, and after washing, radioactivity of each well was measured by a gamma counter (Beckman Gamma 9000, Beckman Instruments, Fullerton, Calif.). Of 216 hybridoma clones, 32 hybridoma clones were positive in the IL-6 binding assay. From among these clones, finally MH166.BSF2, a stable clone, was selected. Anti-IL-6 antibody MH166 has a subtype of IgG1 κ type.

Then, using a IL-6-dependent mouse hybridoma clone MH60.BSF2, a neutralizing activity with regard to the growth of the hybridoma by MH166 antibody was investigated. MH60.BSF2 cells were aliquoted to $1\times10^4$/200 μl/well, to which a sample containing MH166 antibody was added, and cultured for 48 hours. After adding 0.5 μCi/well of $^3$H-thymidine (New England Nuclear, Boston, Mass.), culturing was continued for further six hours. The cells were placed on a glass filter paper, and were treated by an automated harvester (Labo Mash Science Co., Tokyo, Japan). As the control, rabbit anti-IL-6 antibody was used.

As a result, MH166 antibody inhibited $^3$H-thymidine incorporation by MH60.BSF2 cells induced by IL-6 in a dose dependent manner. This revealed that MH166 antibody neutralizes the activity of IL-6.

Reference Example 3

Preparation of Anti-human IL-6 Receptor Antibody

Anti-IL-6 receptor antibody MT18 prepared by the method of Hirata et al. (Hirata, Y. et al., J. Immunol. (1989) 143, 2900-2906) was conjugated to a CNBr-activated Sepharose 4B (manufactured by Pharmacia Fine Chemicals, Piscataway, N.J.) to purify IL-6 receptor (Yamasaki et al., Science (1988) 241, 825-828). A human myeloma cell line U266 was solubilized with 1 mM p-paraaminophenylmethanesulfonyl fluoride hydrochloride (manufactured by Wako Pure Chemicals) (digitonin buffer) containing 1% digitonin (manufactured by Wako Pure Chemicals), 10 mM triethanolamine (pH 7.8), and 0.15 M NaCl, and was mixed with MT18 antibody conjugated to Sepharose 4B beads. Subsequently, the beads were washed six times in the digitonin buffer to prepare a partially purified IL-6 receptor.

BALB/c mice were immunized with the above partially purified IL-6 receptor obtained from $3\times10^9$ U266 cells four times every ten days, and then a hybridoma was prepared according to a standard method. The culture supernatant of the hybridoma from growth-positive wells were examined for the biding activity to IL-6 receptor in the following manner. $5\times10^7$ U266 cells were labelled with $^{35}$S-methionine (2.5 mCi), and were solubilized with the above digitonin buffer. The solubilized U266 cells were mixed with 0.04 ml of MT18 antibody conjugated to Sepharose 4B beads, and then washed for six times in the digitonin buffer. Using 0.25 ml of the digitonin buffer (pH 3.4), $^{35}$S-methionine-labeled IL-6 receptor was eluted, which was neutralized with 0.025 ml of 1 M Tris, pH 7.4.

0.05 ml of the hybridoma culture supernatant was mixed with 0.01 ml Protein G Sepharose (manufactured by Pharmacia). After washing, the Sepharose was incubated with 0.005 ml solution of $^{35}$S-labeled IL-6 receptor solution. The immunoprecipitated substances were analyzed by SDS-PAGE to study the culture supernatant of hybridoma that reacts with IL-6 receptor. As a result, a reaction-positive hybridoma clone PM-1 was established. Antibody produced from the hybridoma PM-1 had the IgG1 K subtype.

The activity of the antibody produced by the hybridoma PM-1 to inhibit the binding of IL-6 to IL-6 receptor was evaluated using a human myeloma cell line U266. Human recombinant IL-6 was prepared from E. coli (Hirano et al., Immunol. Lett. (1988) 17, 41-45), and was labeled with $^{125}$I using the Bolton-Hunter reagent (New England Nclear, Boston, Mass.) (Taga et al., J. Exp. Med. (1987) 166, 967-981).

$4 \times 10^5$ U266 cells were cultured with a culture supernatant of 70% (v/v) hybridoma PM-1 and 14000 CPM of $^{125}$I-labeled IL-6 for one hour. Seventy microliters of a sample was layered onto 300 µl of FCS in a 400 µl microfuge polyethylene tube, centrifuged, and then the radioactivity of the cells were measured.

The result revealed that the antibody produced by the hybridoma PM-1 inhibits the binding of IL-6 to IL-6 receptor.

Reference Example 4

Preparation of Anti-mouse IL-6 Receptor Antibody

A monoclonal antibody against mouse IL-6 receptor was prepared by the method of Saito, T. et al., J. Immunol. (1991) 147, 168-173.

CHO cells that produce soluble mouse IL-6 receptor were cultured in an IMDM culture medium supplemented with 10% FCS. From the culture supernatant, soluble mouse IL-6 receptor was purified using an affinity column in which anti-mouse IL-6 receptor antibody RS12 (see the above Saito, T. et al.) was immobilized to the Affigel 10 gel (manufactured by Biorad).

Fifty µg of soluble mouse IL-6 receptor thus obtained was mixed with Freund's complete adjuvant, which was intraperitoneally injected to the abdomen of Wistar rats. Two weeks later, the rats received booster immunization with Freund's incomplete adjuvant. On day 45, spleen cells were removed from the rats, and $2 \times 10^8$ of the cells were subjected to cell fusion with $1 \times 10^7$ mouse myeloma cells P3U1 with 50% PEG1500 (manufactured by Boehringer Mannheim) using a standard method, and the hybridoma were then screened with the HAT medium.

After adding the culture supernatant to a plate coated with rabbit anti-rat IgG antibody (manufactured by Cappel), soluble mouse IL-6 receptor was reacted thereto. Then, using an ELISA method employing rabbit anti-mouse IL-6 receptor antibody and alkaline phosphatase-labelled sheep anti-rabbit IgG, hybridomas that produce antibodies against soluble mouse IL-6 receptor were screened. The hybridoma clones for which antibody production was confirmed were subjected to subscreening twice to obtain a single hybridoma clone. This clone was designated as MR16-1.

A neutralizing activity in signal transduction of mouse IL-6 by the antibody produced by this hybridoma was examined using $^3$H-thymidine incorporation that employs MH60.BSF2 cells (Matsuda, T. et al., J. Immunol. (1988) 18, 951-956). To a 96-well plate, MH60.BSF2 cells were prepared to $1 \times 10^4$ cells/200 µl/well. To this plate were added 10 pg/ml of mouse IL-6 and MR16-1 antibody or RS12 antibody at 12.3-1000 ng/ml, and cultured at 37° C. in 5% $CO_2$ for 44 hours, followed by the addition of 1 µCi/well of $^3$H-thymidine. Four hours later, the incorporation of $^3$H-thymidine was measured. As a result, MR16-1 antibody inhibited the $^3$H-thymidine incorporation by MH60.BSF2 cells.

Thus, it was revealed that antibody produced by the hybridoma MR16-1 (FERM BP-5874) inhibits the binding of IL-6 to IL-6 receptor.

The invention claimed is:

1. A method for treatment of adult-onset Still's disease, comprising administering an antibody against an IL-6 receptor to a patient who needs said treatment, wherein the antibody against the IL-6 receptor is an antibody which inhibits binding of IL-6 to the IL-6 receptor by binding to the IL-6 receptor.

2. A method according to claim 1, wherein the antibody against the IL-6 receptor is a monoclonal antibody.

3. A method according to claim 2, wherein the monoclonal antibody is a monoclonal antibody against the human IL-6 receptor.

4. A method according to claim 1, wherein the antibody against the IL-6 receptor is a recombinant antibody.

5. A method according to claim 3, wherein the monoclonal antibody against the human IL-6 receptor is the PM-1 antibody (FERM BP-2998) or a humanized or chimeric version thereof.

6. A method according to claim 1, wherein the antibody against a IL-6 receptor is a chimeric antibody, humanized antibody or a human antibody.

7. A method according to claim 6, wherein the humanized antibody is a humanized variant of PM-1 antibody (FERM BP-2998).

8. A method according to claim 1, wherein the antibody is administered to the patient at a dose of 0.5 to 40 mg per kilogram of body weight every four weeks.

9. A method according to claim 7, wherein the antibody is administered to the patient at a dose of 0.5 to 40 mg per kilogram of body weight every four weeks.

* * * * *

UNITED STATES PATENT AND TRADEMARK OFFICE
CERTIFICATE OF CORRECTION

| | | |
|---|---|---|
| PATENT NO. | : 7,955,598 B2 | Page 1 of 1 |
| APPLICATION NO. | : 11/704233 | |
| DATED | : June 7, 2011 | |
| INVENTOR(S) | : Yoshizaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 589 days.

Signed and Sealed this
Twenty-ninth Day of January, 2013

David J. Kappos
*Director of the United States Patent and Trademark Office*